United States Patent
Suzuki

(10) Patent No.: US 8,681,933 B2
(45) Date of Patent: Mar. 25, 2014

(54) X-RAY COMPUTED TOMOGRAPHY APPARATUS

(71) Applicants: Kabushiki Kaisha Toshiba, Minato-ku (JP); Toshiba Medical Systems Corporation, Otawara (JP)

(72) Inventor: Tatsuro Suzuki, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/771,122

(22) Filed: Feb. 20, 2013

(65) Prior Publication Data

US 2013/0177129 A1 Jul. 11, 2013

Related U.S. Application Data

(63) Continuation of application No. PCT/JP2012/080966, filed on Nov. 29, 2012.

(30) Foreign Application Priority Data

Dec. 1, 2011 (JP) .................................. 2011-263791

(51) Int. Cl.
- *H05G 1/02* (2006.01)
- *H05G 1/70* (2006.01)
- *G21K 5/10* (2006.01)

(52) U.S. Cl.
USPC ................................ 378/20; 378/92; 378/146

(58) Field of Classification Search
USPC ........... 378/4–20, 91–96, 145, 146, 204, 209, 378/210, 901
See application file for complete search history.

(56) References Cited

U.S. PATENT DOCUMENTS

| 5,412,562 | A | 5/1995 | Nambu et al. |
| 2005/0175143 | A1* | 8/2005 | Miyazaki et al. ............... 378/19 |
| 2007/0217567 | A1* | 9/2007 | Noshi et al. ....................... 378/4 |
| 2009/0092224 | A1 | 4/2009 | Nishide et al. |

FOREIGN PATENT DOCUMENTS

| JP | 06-078916 A | 3/1994 |
| JP | 2009-089760 A | 4/2009 |
| JP | 2009-261942 | 11/2009 |
| JP | 2010-268827 A | 12/2010 |

OTHER PUBLICATIONS

International Search Report mailed Jan. 29, 2013 in PCT/JP2012/080966 filed Nov. 29, 2012.
International Written Opinion mailed Jan. 29, 2013 in PCT/JP2012/080966 filed Nov. 29, 2012.

* cited by examiner

*Primary Examiner* — Anastasia Midkiff
(74) *Attorney, Agent, or Firm* — Oblon, Spivak, McClelland, Maier & Neustadt, L.L.P.

(57) ABSTRACT

According to one embodiment, an X-ray computed tomography apparatus includes an X-ray tube to generate X-rays, X-ray detector to detect the X-rays transmitted through an object, top to place the object, rotation driving unit to rotate a rotating frame with the X-ray tube and the X-ray detector around the object, movement driving unit to relatively reciprocate the rotating frame and the top over a plurality of times along a long-axis direction of the top, and scan control unit to control the movement driving unit in the relative reciprocal movement such that moving loci of the X-ray tube corresponding to the respective forward movements are matched with each other and moving loci of the X-ray tube corresponding to the respective backward movements are matched with each other.

6 Claims, 16 Drawing Sheets

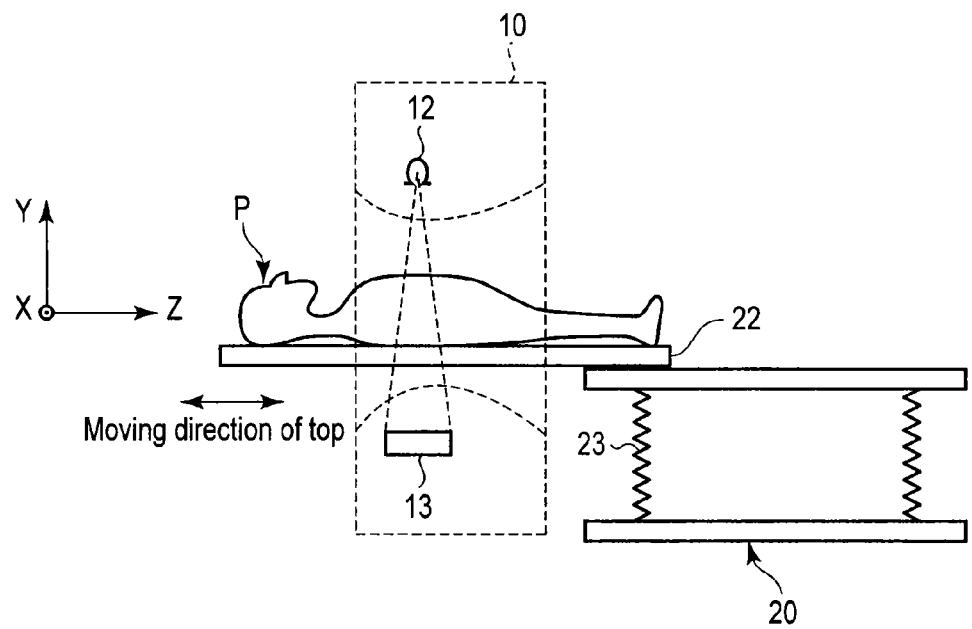
F I G. 2
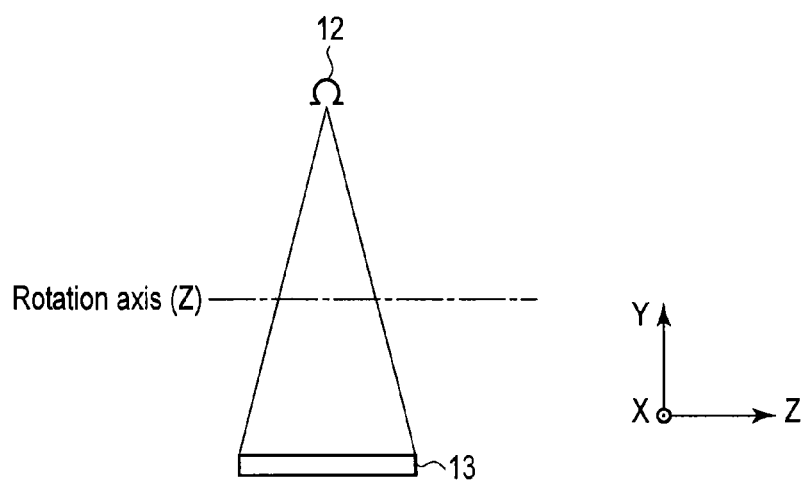
F I G. 3

(With constant velocity and constant acceleration)

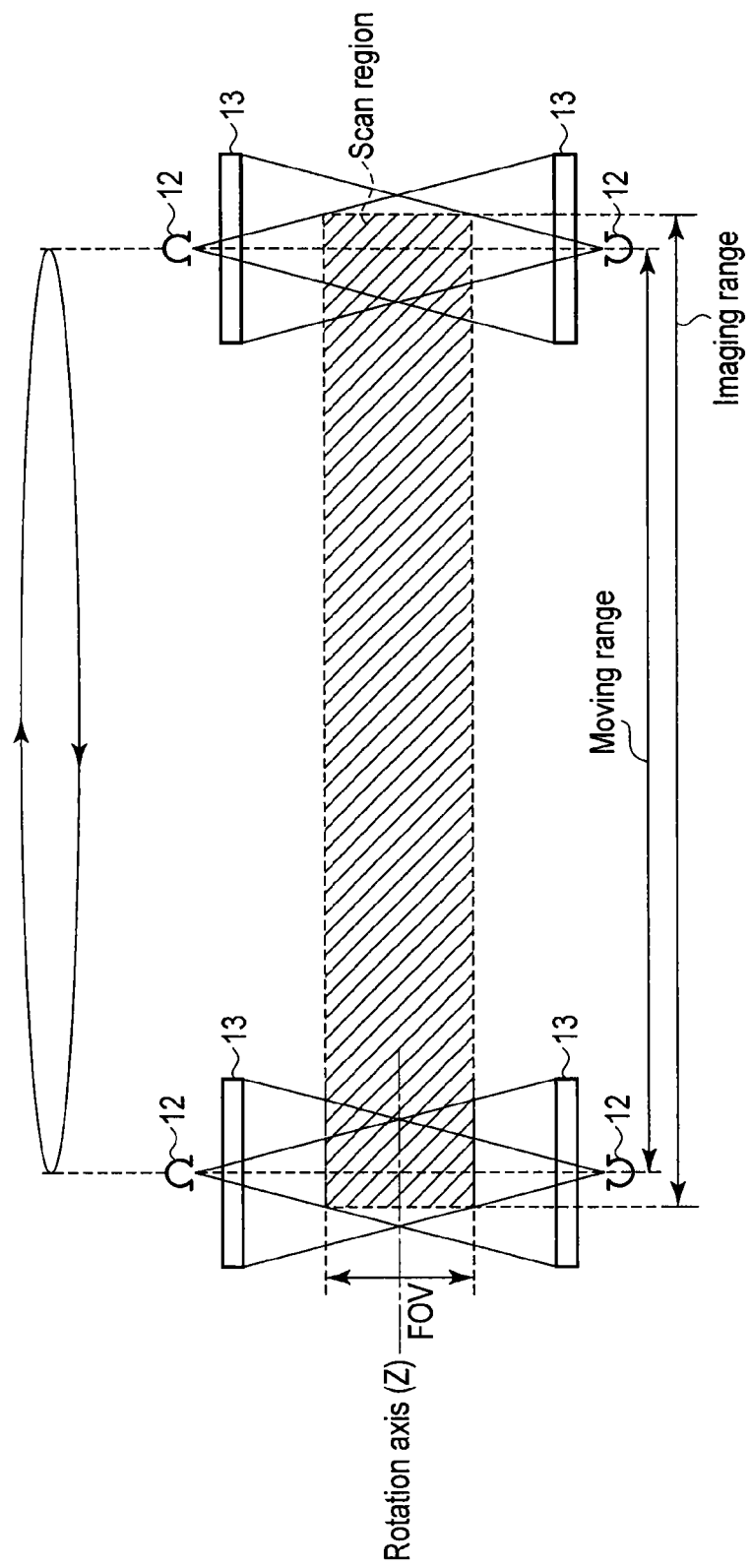
F I G. 12

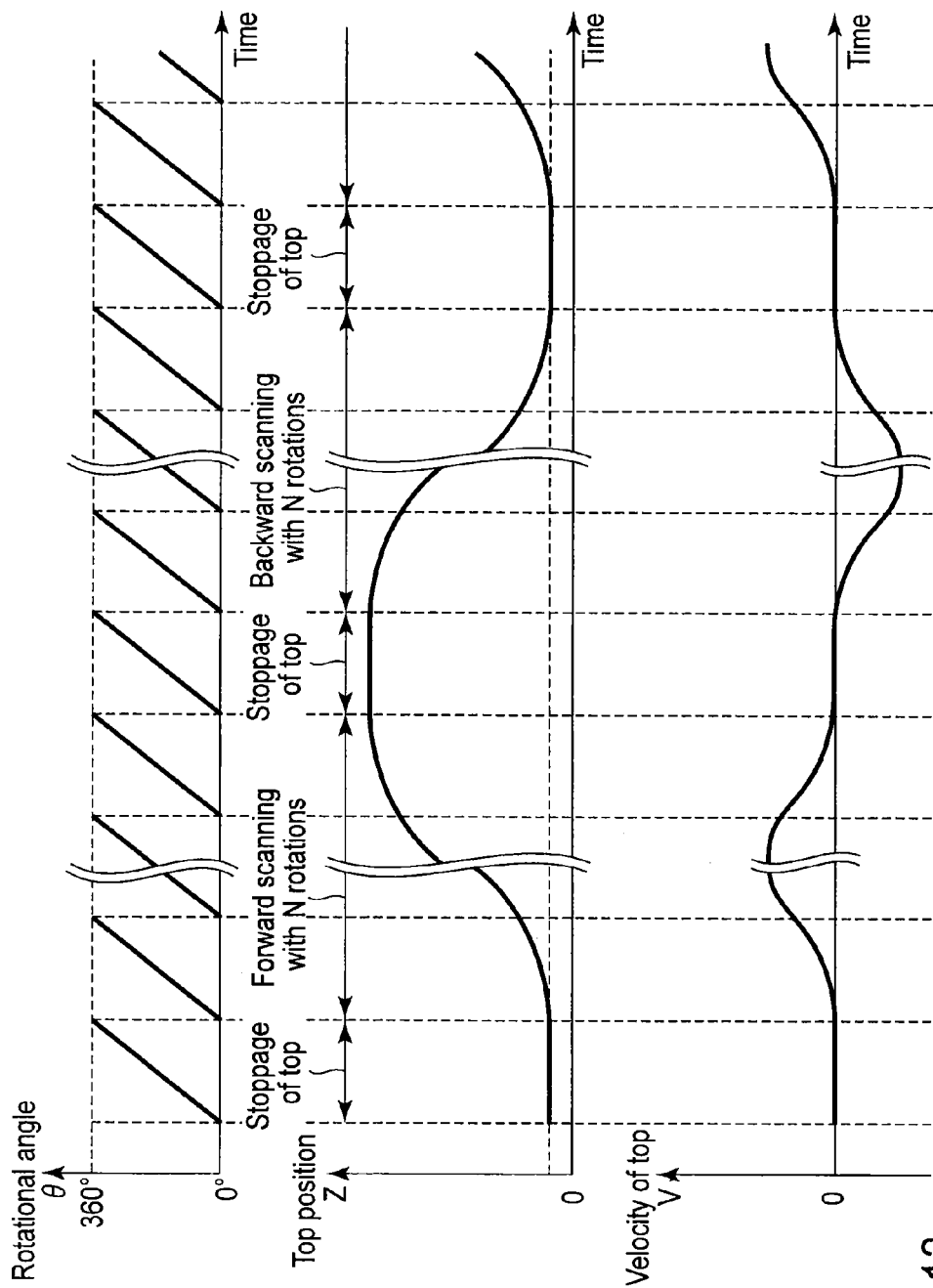
F I G. 13

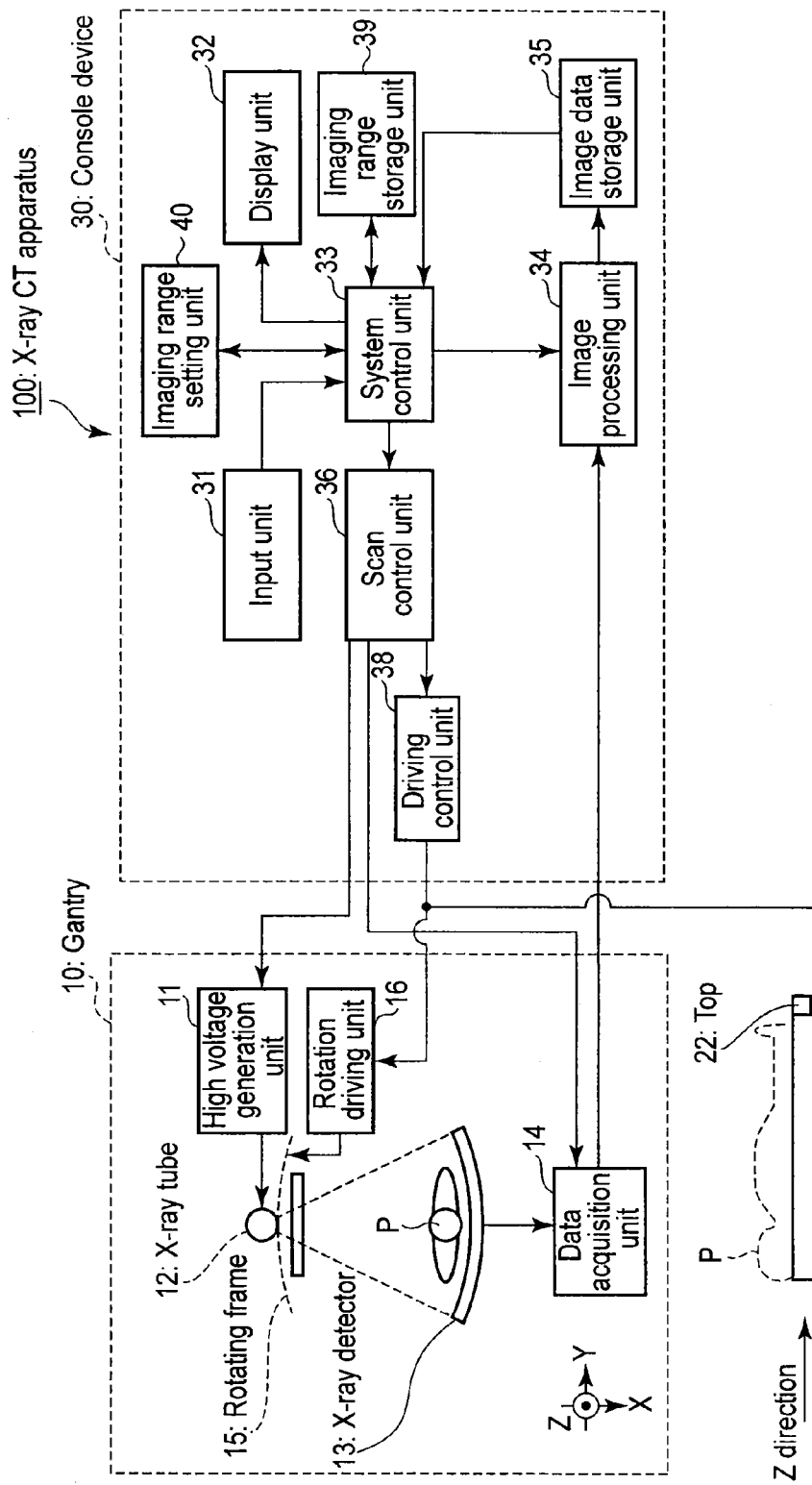
F I G. 15

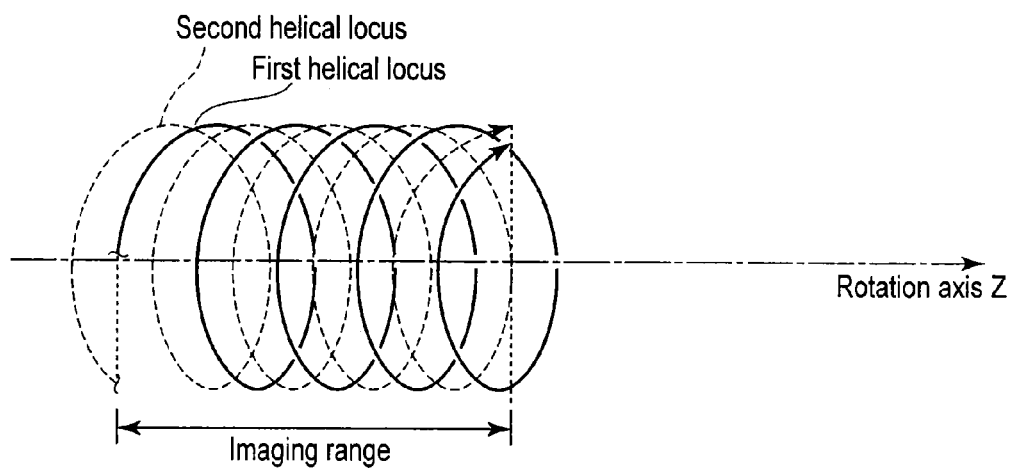
F I G. 20

US 8,681,933 B2

X-RAY COMPUTED TOMOGRAPHY APPARATUS

CROSS REFERENCE TO RELATED APPLICATIONS

This application is a Continuation Application of PCT Application No. PCT/JP2012/080966, filed Nov. 29, 2012 and based upon and claiming the benefit of priority from Japanese Patent Application No. 2011-263791, filed Dec. 1, 2011, the entire contents of all of which are incorporated herein by reference.

FIELD

Embodiments described herein relate generally to an X-ray computed tomography apparatus.

BACKGROUND

Reciprocal helical scanning is recently available as one of the scanning schemes using an X-ray computed tomography apparatus (to be referred to as an X-ray CT apparatus hereinafter). Reciprocal helical scanning is an imaging technique of continuously reciprocating the top while continuously rotating the X-ray tube on a circular orbit centered on an object to be examined. With regard to the reciprocal movement of the top, imaging along a forward path will be referred to as forward scanning hereinafter. With regard to the reciprocal movement of the top, imaging along a backward path will be referred to as backward scanning.

According to reciprocal helical scanning, the X-ray tube (or the X-ray detector) traces a locus in a helical form (to be referred to as a helical locus hereinafter) with respect to an object. This will obtain a tomographic image with excellent continuity in a wide range. For example, reciprocal helical scanning on an object injected with a contrast medium is used to analyze hemodynamics (perfusion).

Conventional reciprocal helical scanning, however, has the following problems. First, the object is not imaged during a returning process from forward (backward) scanning to backward (forward) scanning, i.e., an acceleration/deceleration process of the top (for example, FIG. 19). An imaging wait time during an acceleration/deceleration process of the top degrades the temporal resolution in perfusion analysis. Second, X-rays are emitted when the top reaches a constant velocity while the rotating frame on which the X-ray tube and the X-ray detector are mounted is rotated in advance at a predetermined angular velocity. For this reason, different helical loci are sometimes traced in different forward (backward) scans (for example, FIG. 20). The differences between helical loci in different forward (backward) scans cause differences in image quality (to be referred to as image quality differences hereinafter) concerning the same imaging position in the object. If the temporal resolution is low and image quality differences occur at the same imaging position, perfusion analysis sometimes becomes inaccurate.

BRIEF DESCRIPTION OF THE DRAWINGS

FIG. 2 is a sectional view showing an example of sections of the gantry and bed of the X-ray computed tomography apparatus according to this embodiment.

FIG. 3 is a view showing the definitions of axes according to this embodiment.

FIG. 12 is a view showing an example of the positional relationship between the X-ray tube, the X-ray detector, and the imaging range in reciprocal helical scanning according to this embodiment.

FIG. 13 is a graph showing an example of the time dependencies on the rotational angle of the X-ray tube, the position of the top, and the velocity of the top according to this embodiment.

FIG. 15 is a view showing the arrangement of an X-ray computed tomography apparatus according to a modification of this embodiment.

FIG. 20 is a view showing an example of a helical locus for each forward path in conventional reciprocal helical scanning.

DETAILED DESCRIPTION

Figure 1:
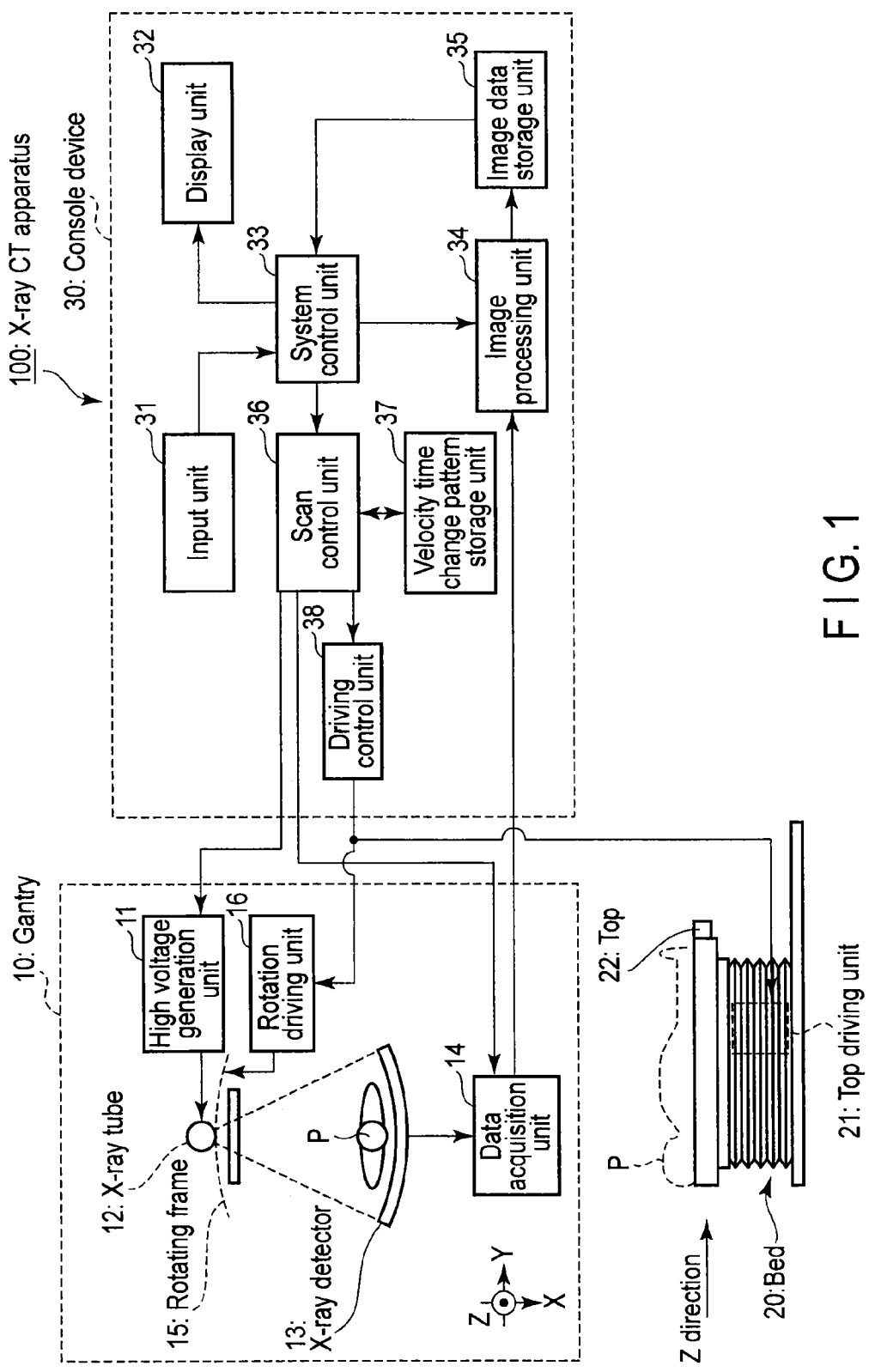
FIG. 1 is a view showing the arrangement of an X-ray computed tomography apparatus according to an embodiment.

In general, according to one embodiment, an X-ray computed tomography apparatus includes an X-ray tube, an X-ray detector, a top, a rotation driving unit, a movement driving unit, and a scan control unit. The X-ray tube generates X-rays. The X-ray detector detects the X-rays generated from the X-ray tube and transmitted through an object. The object is placed on the top. The rotation driving unit rotates a rotating frame around the object, wherein the X-ray tube and the X-ray detector are mounted on the rotating frame. The movement driving unit relatively reciprocates the rotating frame and the top over a plurality of times along a long-axis direction of the top. The scan control unit controls the movement driving unit in relative reciprocal movement of the rotating frame and the top such that a plurality of moving loci of the X-ray tube corresponding to a plurality of respective forward movements are matched with each other and a plurality of moving loci of the X-ray tube corresponding to a plurality of respective backward movements are matched with each other.

An X-ray computed tomography apparatus (to be referred to as an X-ray CT apparatus hereinafter) according to an embodiment will be described below with reference to the accompanying drawing.

X-ray CT apparatuses include various types of apparatuses, e.g., a rotate/rotate-type apparatus in which an X-ray tube and an X-ray detector rotate together around an object, and a stationary/rotate-type apparatus in which many X-ray detection elements are arrayed in the form of a ring, and only an X-ray tube rotates around an object. This embodiment can be applied to either type. Recently, with advances toward the commercialization of a so-called multi-tube type X-ray computed tomography apparatus having a plurality of pairs of X-ray tubes and X-ray detectors mounted on a rotating frame, related techniques have been developed. This embodiment can be applied to both a conventional single-tube type X-ray computed tomography apparatus and a multi-tube type X-ray computed tomography apparatus. The single-tube, rotate-rotate-type X-ray computed tomography apparatus will be exemplified here.

Note that the same reference numerals denote constituent elements having almost the same functions and arrangements in the following description, and a repetitive description will be made only when required.

FIG. 1 is a view showing the arrangement of an X-ray CT apparatus 100 according to this embodiment. As shown in FIG. 1, the X-ray CT apparatus 100 includes a gantry 10, a bed 20, and a console device 30. FIG. 2 is a sectional view showing an example of sections of the gantry 10 and bed 20 of the X-ray CT apparatus 100. The gantry 10 and the bed 20 are arranged in the manner exemplified by FIG. 2. An arrow shown in FIG. 2 indicates the body axis direction of an object P. A top 22 continuously reciprocates in the first direction (e.g., the forward direction) parallel to the body axis direction of the object P and the second direction (e.g., the backward direction) opposite to the first direction.

As shown in FIGS. 1 and 2, an annular or disk-like rotating frame 15 is mounted on the gantry 10. The rotating frame 15 supports an X-ray tube 12 and an X-ray detector 13 so as to allow them to rotate around the rotation axis. The rotating frame 15 supports the X-ray tube 12 and the X-ray detector 13 so as to make them face each other through the object P. The rotating frame 15 is connected to a rotation driving unit 16.

The rotation driving unit 16 continuously rotates the rotating frame 15 under the control of the control circuit 38 in the console device 30. The X-ray tube 12 and the X-ray detector 13, which are supported on the rotating frame 15, rotate around the rotation axis.

The definitions of the axes according to this embodiment will be described with reference to FIG. 3. The Z-axis is defined as the rotation axis of the rotating frame 15. The Y-axis is defined as an axis connecting the X-ray focus of the X-ray tube 12 and the center of the X-ray detection surface of the X-ray detector 13. The Y-axis is perpendicular to the Z-axis. The X-axis is defined as an axis perpendicular to the Y- and Z-axes. In this manner, the XYZ orthogonal coordinate system forms a rotating coordinate system which rotates with the rotation of the X-ray tube 12.

The X-ray tube 12 generates an X-ray cone beam upon receiving a high voltage applied from a high voltage generation unit 11. The high voltage generation unit 11 applies a high voltage to the X-ray tube 12 under the control of a scan control unit 36.

The X-ray detector 13 detects the X-rays generated from the X-ray tube 12 and transmitted through the object P. The X-ray detector 13 generates a current signal corresponding to the intensity of the detected X-rays. It is preferable to use, as the X-ray detector 13, a type called a flat panel detector or multi-row detector. An X-ray detector of this type has a plurality of X-ray detection elements arrayed two-dimensionally. Assume that in the following description, a single X-ray detection element forms a single channel. For example, 100 X-ray detection elements are arrayed one-dimensionally along an arc direction (channel direction) with the X-ray focus being the center and the distance from the center to the center of the light-receiving unit of each X-ray detection element being the radius. The plurality of X-ray detection elements arrayed along the channel direction will be referred to as an X-ray detection element row. For example, 64 X-ray detection element rows are arrayed along the slice direction indicated by the Z-axis. A data acquisition unit (data acquisition system to be referred to as a DAS hereinafter) 14 is connected to the X-ray detector 13.

As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor such as selenium by X-rays and migration of the electron-hole pairs to an electrode, i.e., a photoconductive phenomenon. As an X-ray detection element, either of these schemes can be used.

The data acquisition unit 14 reads an electrical signal from the X-ray detector 13 for each channel under the control of the scan control unit 36. The data acquisition unit 14 amplifies the read signals. The data acquisition unit 14 generates projection data by converting the amplified electrical signals into digital signals. Note that the data acquisition unit 14 can also generate projection data by reading electrical signals from the X-ray detector 13 during a period in which no X-rays are emitted. The generated projection data is supplied to the console device 30 via a noncontact data transmission unit (not shown).

The bed 20 is installed near the gantry 10. The bed 20 includes the top 22, a top support mechanism 23, and a top driving unit 21. The object P is placed on the top 22. The top support mechanism 23 supports the top 22 so as to allow it to reciprocate along the Z-axis. Typically, the top support mechanism 23 supports the top 22 so as to make the long axis of the top 22 parallel to the Z-axis. The top driving unit 21 drives the top 22 under the control of a driving control unit 38 of the console device 30 (to be described later). More specifically, the top driving unit 21 moves the top 22 at a constant velocity in a constant-velocity region set in an imaging range. The top driving unit 21 accelerates or decelerates the moving velocity of the top 22 in an acceleration/deceleration region in the imaging range. That is, the top driving unit 21 decelerates and stops the top 22 in a deceleration region. After the top 22 stops, the top driving unit 21 reverses the moving direction of the top 22. The top driving unit 21 accelerates the moving velocity of the top 22 in an acceleration region.

Note that the gantry 10 may be moved at a constant velocity instead of the top 22. A gantry driving unit (not shown) moves the gantry 10 along the Z-axis. In addition, the gantry driving unit accelerates or decelerates the gantry 10 in the above acceleration/deceleration region. That is, the gantry driving unit decelerates and stops the gantry 10 in a deceleration region. After the gantry 10 stops, the gantry driving unit reverses the moving direction of the gantry 10. The gantry driving unit accelerates the moving velocity of the gantry 10 in an acceleration region.

The console device 30 includes an input unit 31, a display unit 32, a system control unit 33, an image processing unit 34, an image data storage unit 35, a scan control unit 36, a velocity time change pattern storage unit 37, and the driving control unit 38.

The input unit 31 includes input devices such as a mouse, keyboard, and touch panel. The input unit 31 inputs, to the X-ray CT apparatus 100, various kinds of commands, various kinds of information, and the like input by the operator via input devices. The display unit 32 is a display such as an LCD (Liquid Crystal Display). The display unit 32 displays a medical image stored in the image data storage unit 35 (to be described later), a GUI (Graphical User Interface) for accepting various kinds of instructions from the operator, and the like. The input unit 31 sets or inputs various kinds of scan conditions in reciprocal helical scanning in accordance with instructions input by the operator via input devices. Reciprocal helical scanning is an imaging technique of continuously reciprocating the top 22 while continuously rotating the X-ray tube 12 on a circular orbit centered on an object to be examined.

Scan conditions include, for example, an imaging range for an object for which reciprocal helical scanning is executed, the position information of the imaging range, the velocity of the top 22 (to be referred to as the top velocity hereinafter) concerning reciprocal helical scanning, a helical pitch, a scan time, the rotational velocity of the rotating frame 15, and the distance of a constant-velocity interval of the top 22. Note that the input unit 31 may input a range, of the imaging range, in which the top 22 is moved at a constant velocity by operation by the operator via an input device. The input unit 31 may also input an angular velocity at which the rotating frame 15 is continuously rotated around the rotation axis in accordance with an instruction from the operator via an input device. Note that the scan control unit 36 (to be described later) may set an angular velocity in advance based on scan conditions.

Figure 4:
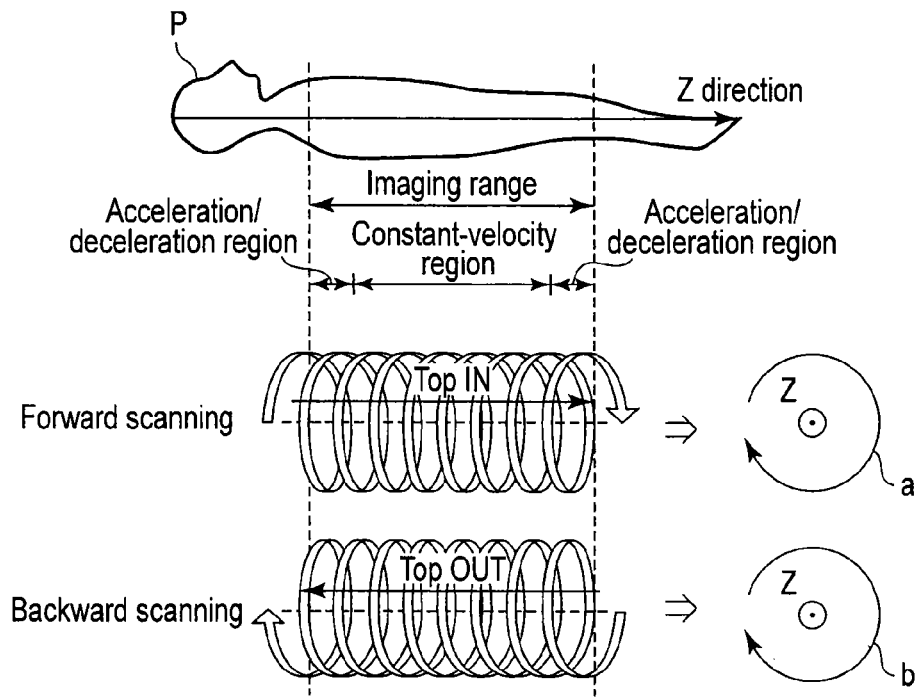
FIG. 4 is a view for explaining reciprocal helical scanning according to this embodiment.

FIG. 4 is a view for explaining reciprocal helical scanning. According to reciprocal helical scanning, as exemplified by FIG. 4, the focus of the X-ray tube 12 (or the X-ray detector 13) traces a locus in a helical form (to be referred to as a helical locus hereinafter) with respect to the object P. As exemplified by FIG. 4, of the body axis direction of the object P, the direction of an arrow from the head of the object to the feet is defined as a Z direction. Imaging performed by moving the top 22 in the same direction as the Z direction will be referred to as forward scanning. Imaging performed by moving the top 22 in a direction opposite to the Z direction will be referred to as backward scanning. The arrow of "top IN" exemplified in FIG. 4 indicates a direction in which the top 22 is moved in forward scanning. The arrow of "top OUT" exemplified in FIG. 4 indicates a direction in which the top 22 is moved in backward scanning. The arrows of symbols a and b shown in FIG. 4 indicate the rotating direction of the X-ray tube 12.

The system control unit 33 includes integrated circuits such as an ASIC (Application Specific Integrated Circuit) and FPGA (Field Programmable Gate Array) and electronic circuits such as a CPU (Central Processing Unit) and MPU (Micro Processing Unit). More specifically, the system control unit 33 controls the overall X-ray CT apparatus 100 by controlling the gantry 10, the bed 20, and each unit in the console device 30. For example, the system control unit 33 controls the scan control unit 36 to acquire projection data. The system control unit 33 controls the image processing unit 34 (to be described later) to reconstruct a medical image based on projection data. The system control unit 33 outputs the scan conditions input via the input unit 31 to the scan control unit 36.

The image processing unit 34 executes various kinds of processes for the projection data generated by the data acquisition unit 14. More specifically, the image processing unit 34 executes preprocessing such as sensitivity correction for the projection data. The image processing unit 34 reconstructs a medical image based on the reconstruction conditions instructed from the system control unit 33. The image processing unit 34 stores the reconstructed medical image in the image data storage unit 35 (to be described later). In order to reconstruct an image, projection data corresponding to one rotation around an object, i.e., 360°, is required, or (180°+fan angle) projection data is required in the half scan method. This embodiment can be applied to either of these reconstruction schemes.

The image data storage unit 35 includes semiconductor memory devices such as a RAM (Random Access Memory), ROM (Read Only Memory), and flash memory, a hard disk, and an optical disk. The image data storage unit 35 stores the medical image reconstructed by the image processing unit 34.

Figure 5:
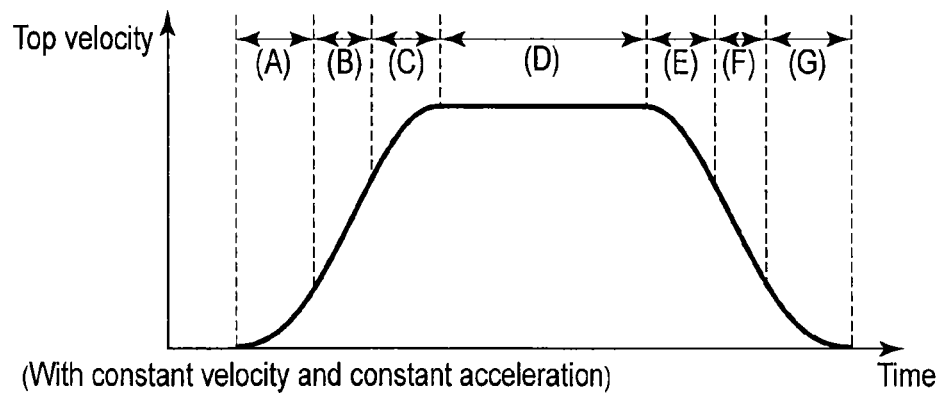
FIG. 5 is a graph showing an example of the relationship between the moving time of the top and the moving velocity of the top in the forward direction according to this embodiment.
Figure 6:
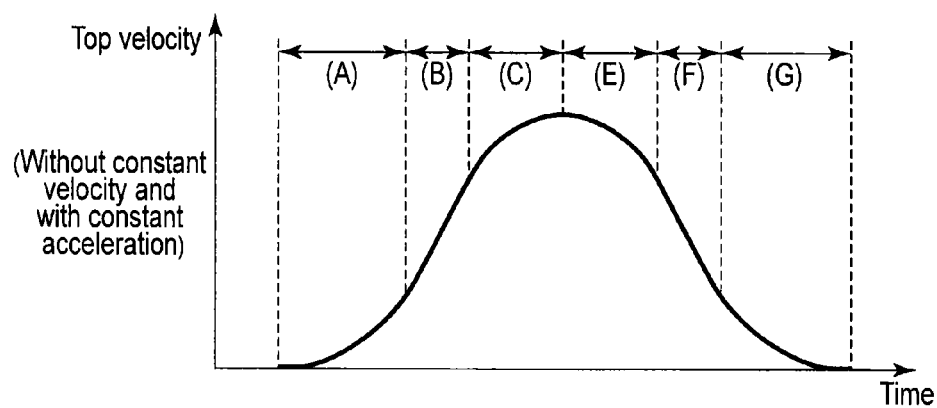
FIG. 6 is a graph showing an example of the relationship between the moving time of the top and the moving velocity of the top in the forward direction according to this embodiment.
Figure 7:
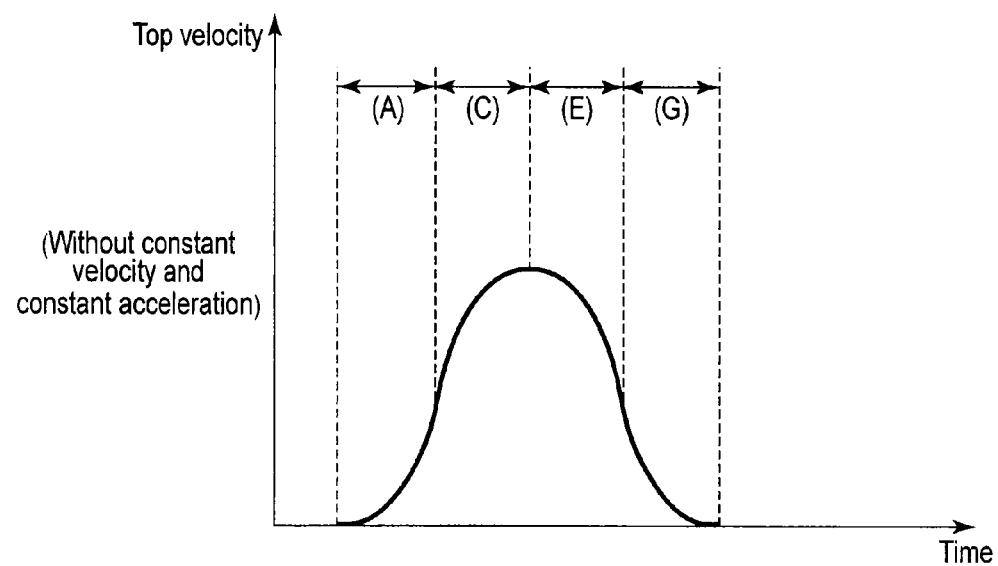
FIG. 7 is a graph showing an example of the relationship between the moving time of the top and the moving velocity of the top in the forward direction according to this embodiment.

The velocity time change pattern storage unit 37 stores a plurality of time change patterns (patterns of acceleration changes) concerning top velocities. FIGS. 5, 6, and 7 each show an example of the relationship between the moving time of the top and the moving velocity of the top (to be referred to as a velocity time change pattern hereinafter) in the forward direction in reciprocal movement of the top 22. FIG. 5 shows a velocity time change pattern associated with values of an imaging range and uniform velocity of the top which are input by the operator. FIG. 7 shows a velocity time change pattern in the case of an imaging range smaller than that in FIG. 5. FIG. 6 shows a velocity time change pattern in the case of an imaging range smaller than that in FIG. 5 but larger than that in FIG. 7.

A time interval (A) in FIGS. 5, 6, and 7 indicates a period during which the acceleration of the top 22 increases. A time interval (B) in FIGS. 5 and 6 indicates a period during which the acceleration of the top 22 is constant. A time interval (C) in FIGS. 5 and 7 indicates a period during which the acceleration of the top 22 decreases. The time intervals (A), (B), and (C) correspond to an acceleration region at a turnaround portion of reciprocal movement in the imaging range.

A time interval (D) in FIG. 5 indicates a period during which the top velocity is constant. The time interval (D) corresponds to a constant-velocity region in the imaging range. A time interval (E) in FIGS. 5, 6, and 7 indicates a period during which the deceleration of the top 22 increases. A time interval (F) in FIGS. 5 and 6 indicates a period during which the deceleration of the top 22 is constant. A time interval (G) in FIGS. 5 and 7 indicates a period during which the deceleration of the top 22 decreases. The time intervals (E), (F), and (G) correspond to a deceleration region at a turnaround portion of reciprocal movement in the imaging range. As indicated by (A), (C), (E), and (G) in FIG. 5, it is possible to reduce the force exerting on the object placed on the top 22 by smoothly changing acceleration while performing acceleration and deceleration.

Note that it is possible to use any type of velocity time change pattern as long as it is a top velocity time change pattern which is set to make the time required for one reciprocal movement of the top 22 become an integer multiple of the time taken to cause the rotating frame 15 to make one rotation around the rotation axis.

The scan control unit 36 includes integrated circuits such as an ASIC and FPGA and electronic circuits such as a CPU and MPU. The scan control unit 36 controls the high voltage generation unit 11, the data acquisition unit 14, and the driving control unit 38 (to be described later) based on the scan conditions instructed from the system control unit 33. For example, the scan control unit 36 reads out a top velocity time change pattern from the velocity time change pattern storage unit 37 based on scan conditions. The scan control unit 36 outputs the readout top velocity time change pattern and scan conditions to the driving control unit 38. The scan control unit 36 outputs an instruction to rotate the rotating frame 15 to the driving control unit 38 based on the scan conditions.

The scan control unit 36 controls the high voltage generation unit 11 to reduce radiation exposure on the object. For example, the scan control unit 36 controls the high voltage generation unit 11 to change X-ray intensities in the direction along the Z-axis (to be referred to as the Z direction hereinafter) and the directions along the X- and Y-axes (to be referred to as the X and Y directions hereinafter) based on a scanogram acquired in advance.

The scan control unit 36 controls the data acquisition unit 14 to acquire projection data. More specifically, the scan control unit 36 controls the data acquisition unit 14 to set the same number of views required to reconstruct a tomographic image at any Z positions in each of forward scanning and backward scanning.

Note that the scan control unit 36 can also calculate the total rotational angle of the top 22 in a constant-velocity interval based on the distance of the contrast-velocity interval and the rotational velocity of the rotating frame 15 which are set or input via the input unit 31. This allows the scan control unit 36 to calculate the rotational angle of the X-ray tube 12 at the end position in the constant-velocity interval based on the set scan conditions. The scan control unit 36 can also set the rotational angle of the X-ray tube 12 at a scan start position on a forward path in a constant-velocity interval of the top 22 to a predetermined position. The scan control unit 36 can calculate the rotational angle of the X-ray tube 12 at the end position in a constant-velocity interval of the top 22 on a backward path in a constant-velocity interval in the same manner as described above. These allow the scan control unit 36 to decide the relationship (to be referred to as the helical locus hereinafter) between the rotational angle of the X-ray tube 12 and the position of the top 22 in reciprocal helical scanning. In addition, the scan control unit 36 can control the driving control unit 38 to make the helical locus of the X-ray tube on a forward path of the top 22 in a constant-velocity interval coincide with that on a backward path of the top 22.

The scan control unit 36 can also decide the velocity of the top 22 or gantry 10 in forward scanning and backward scanning based on the imaging range information for an object which is input by the input unit 31. Note that the scan control unit 36 can also decide the acceleration of the top 22 or gantry 10 at a turnaround portion (to be referred to as the first turnaround portion) from forward scanning to backward scanning and at a turnaround portion (to be referred to as the second turnaround portion hereinafter) from backward scanning to forward scanning based on the imaging range information. The scan control unit 36 can also decide the velocity of the top 22 or gantry 10 in a constant-velocity interval in each of forward scanning and backward scanning based on the imaging range information. In addition, the scan control unit 36 can control the X-ray tube 12 and the X-ray detector 13 to acquire projection data by irradiating an object with X-rays in an acceleration/deceleration interval of the top 22 or gantry 10 at the first and second turnaround portions.

Note that the scan control unit 36 can also control the driving control unit 38 to make the rotation end angle of a helical locus at the end position in a forward constant-velocity interval coincide with the rotation start angle of a helical locus at the start position in a backward constant-velocity interval. In addition, the scan control unit 36 may select a velocity pattern in an acceleration/deceleration interval of the top 22 so as to match the rotation end angle of a helical locus at the end position in a forward constant-velocity interval with the rotation start angle of a helical locus at the start position in a backward constant-velocity interval. For example, to match the rotation end angle with the rotation start angle, the scan control unit 36 selects a velocity pattern that satisfies the following relationship. That is, the rotational angle at the time of deceleration (or acceleration) in an acceleration/deceleration interval is equal to ((rotation start angle−rotation end angle)+360°×n rotations)/2.

The driving control unit 38 controls the rotation driving unit 16 and the top driving unit 21 based on the scan conditions output from the scan control unit 36. The driving control unit 38 adjusts a velocity time change pattern based on the imaging range for the object. More specifically, the driving control unit 38 adjusts a velocity time change pattern such that the time required for each of a plurality of reciprocal movements of the top 22 becomes an integer multiple of the time taken to cause the rotating frame to make one rotation around the rotation axis. For example, the driving control unit 38 adjusts at least one of an acceleration change pattern of a velocity time change pattern, a uniform-velocity time, the magnitude of velocity, and the magnitude of acceleration. The driving control unit 38 controls the top driving unit 21 in accordance with the adjusted velocity time change pattern. The driving control unit 38 controls the rotation driving unit 16 to continuously rotate the rotating frame 15. The driving control unit 38 controls the top driving unit 21 so as to match top velocity time change patterns with each other in the respective reciprocal movements. The driving control unit 38 controls the top driving unit 21 so as to null the wait time at the turnaround time point in reciprocal movement of the top 22. Note that the driving control unit 38 may control the top driving unit 21 to change and adjust the acceleration so as to almost null the wait time at the turnaround time point in reciprocal movement of the top 22.

Figure 8:
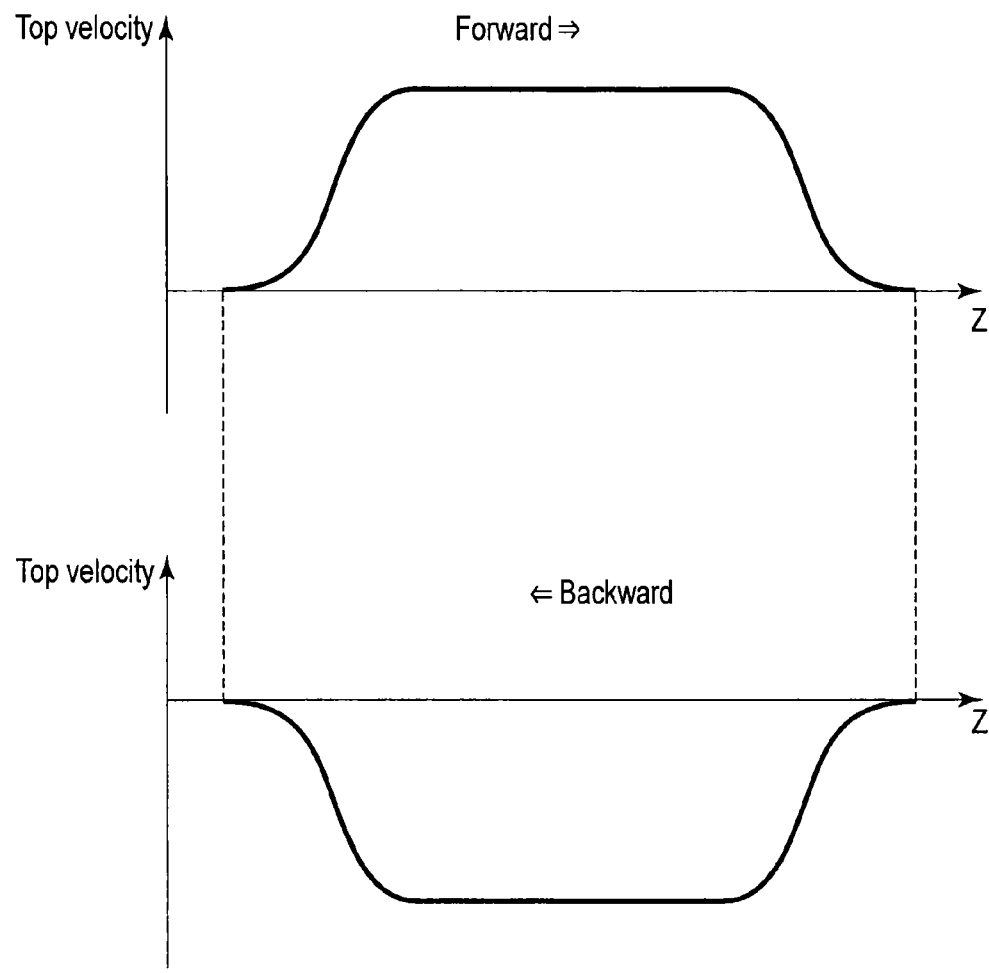
FIG. 8 is a graph showing an example of the relationship between the scan position and the velocity of the top in reciprocal helical scanning according to this embodiment.

FIG. 8 is a graph showing an example of the relationship between the scan position and the top velocity in one reciprocal movement in reciprocal helical scanning. The driving control unit 38 controls the top driving unit 21 to match top velocities with each other in association with the scan position and the scan direction in the respective reciprocal movements, as shown in FIG. 8.

Figure 9:
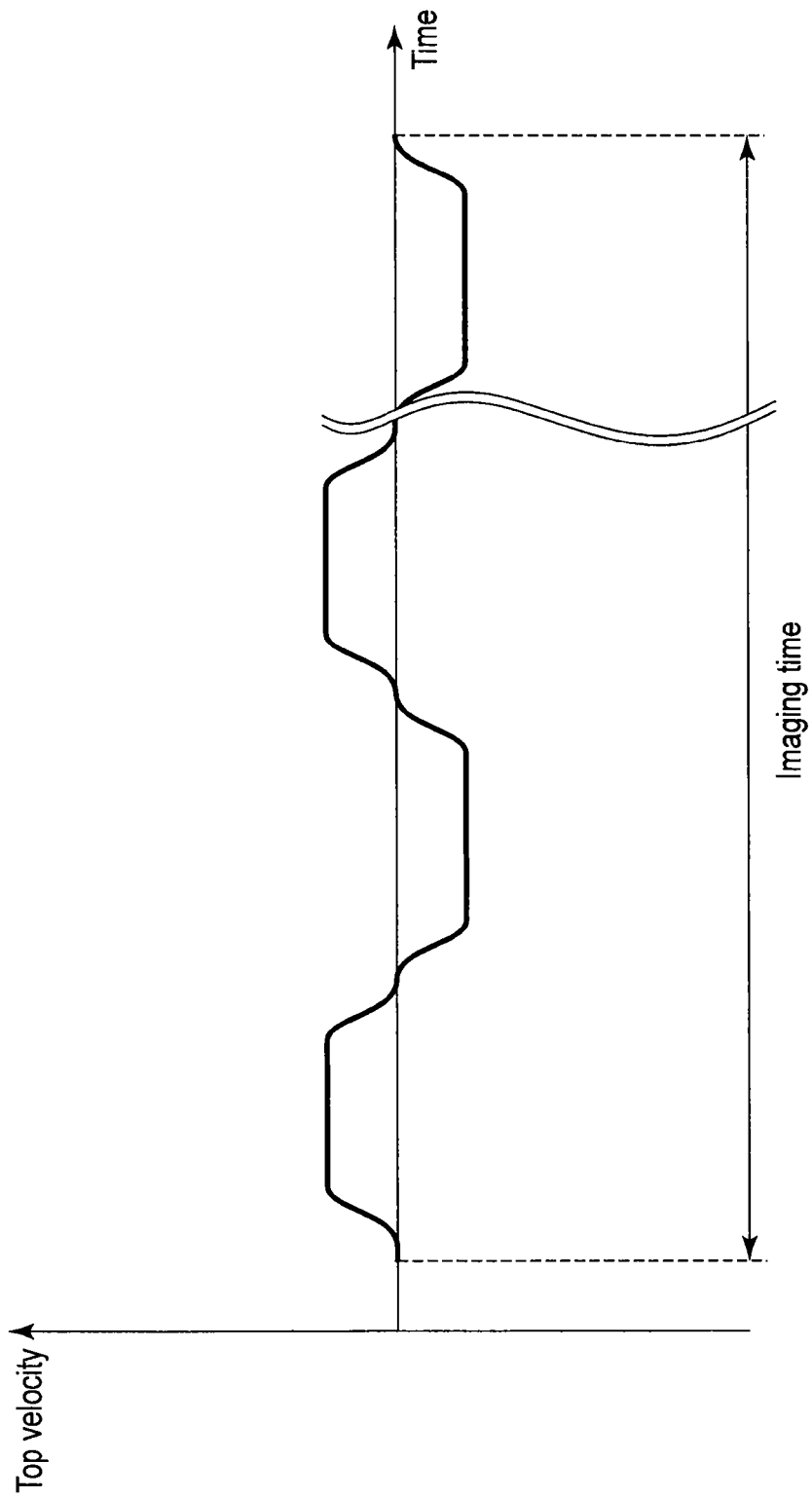
FIG. 9 is a graph showing an example of the relationship between the scan position and the velocity of the top in reciprocal helical scanning without any imaging wait time according to this embodiment.

Note that FIG. 9 is a graph showing an example of the relationship between the scan position and the top velocity in reciprocal helical scanning without any imaging wait time. Note that the driving control unit 38 controls the top driving unit 21 to almost null the imaging wait time (the stop time at a turnaround point) during acceleration/deceleration of the top 22 in each of a plurality of reciprocal movements, as shown in FIG. 9.

In addition, the driving control unit 38 can stop the top 22 at a turnaround point from a forward path to a backward path in each of a plurality of reciprocal movements and execute (180°+fan angle) or 360° imaging under the control of the scan control unit 36. This makes it possible to increase the range of image reconstruction larger than the reciprocal moving range. At this time, the driving control unit 38 controls the top driving unit 21 so as to stop the top 22 during the execution of 360° or (180°+fan angle) imaging using the rotating frame 15 at a turnaround time point.

Figure 10:
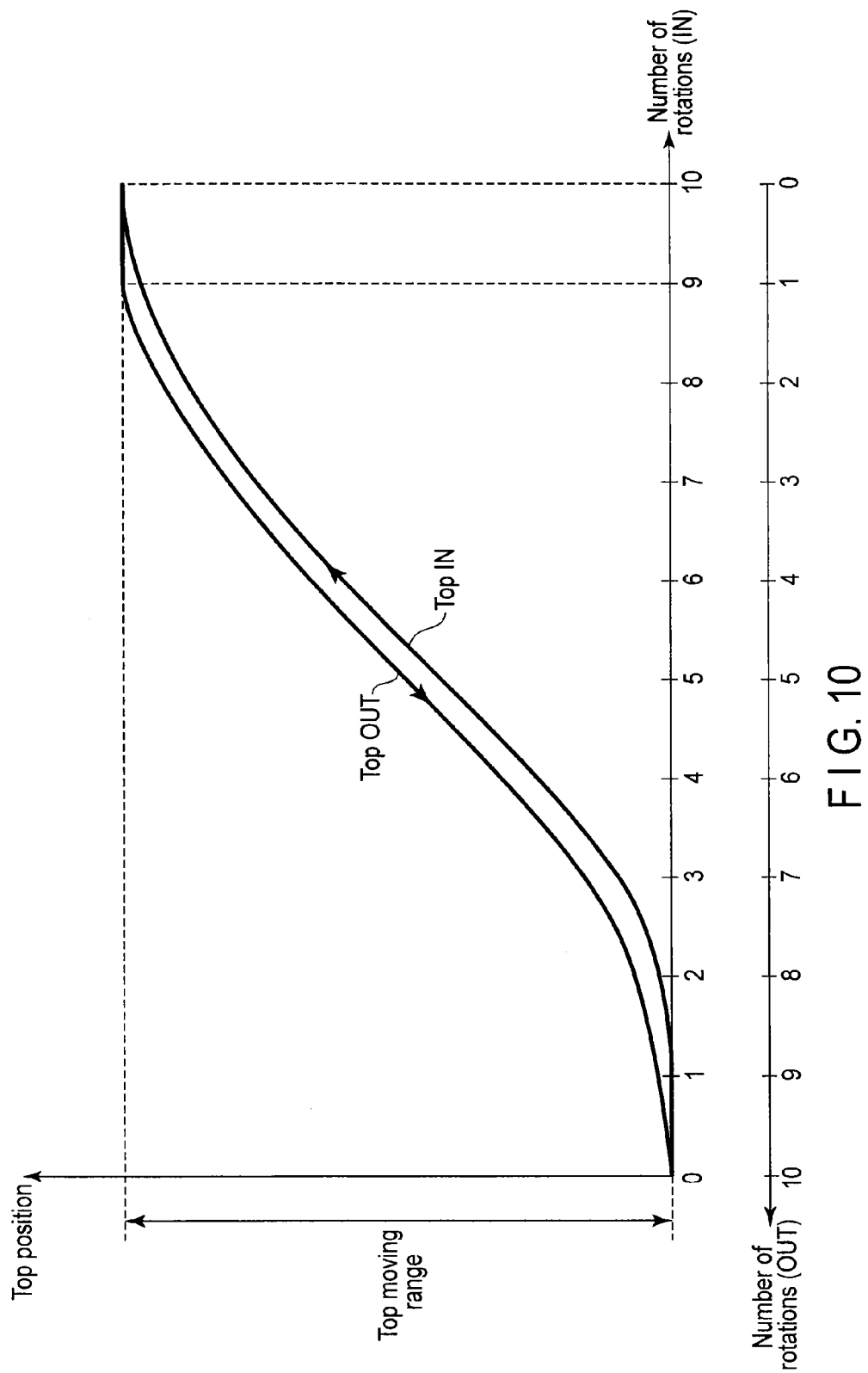
FIG. 10 is a graph showing the relationship between the number of rotations of the X-ray tube and X-ray detector and the position of the top in each moving direction of the top according to this embodiment.

FIG. 10 is a graph showing the relationship between the number of rotations of the rotating frame 15 (or the X-ray tube 12 or the X-ray detector 13) and the position of the top in each moving direction of the top. "Top IN" and "top OUT" in FIG. 10 respectively correspond to "top IN" and "top OUT" in FIG. 4. In "top IN" (forward scanning), the driving control unit 38 controls the top driving unit 21 so as to stop the top 22 until the rotating frame 15 completes one-rotation (360°) imaging. The driving control unit 38 controls the top driving unit 21 so as to accelerate the top 22 upon performing one-rotation (360°) imaging. The driving control unit 38 controls the top driving unit 21 so as to stop the top 22 when the number of rotations of the rotating frame 15 reaches 10. In "top OUT" (backward scanning), the driving control unit 38 controls the top driving unit 21 so as to stop top 22 until the rotating frame 15 completes one-rotation) (360°) imaging. The driving control unit 38 controls the top driving unit 21 so as to accelerate the top 22 upon performing one-rotation (360°) imaging. The driving control unit 38 controls the top driving unit 21 so as to stop the top 22 when the number of rotations of the rotating frame 15 reaches 10. The driving control unit 38 repeats the above control for the top driving unit 21.

Figure 11:
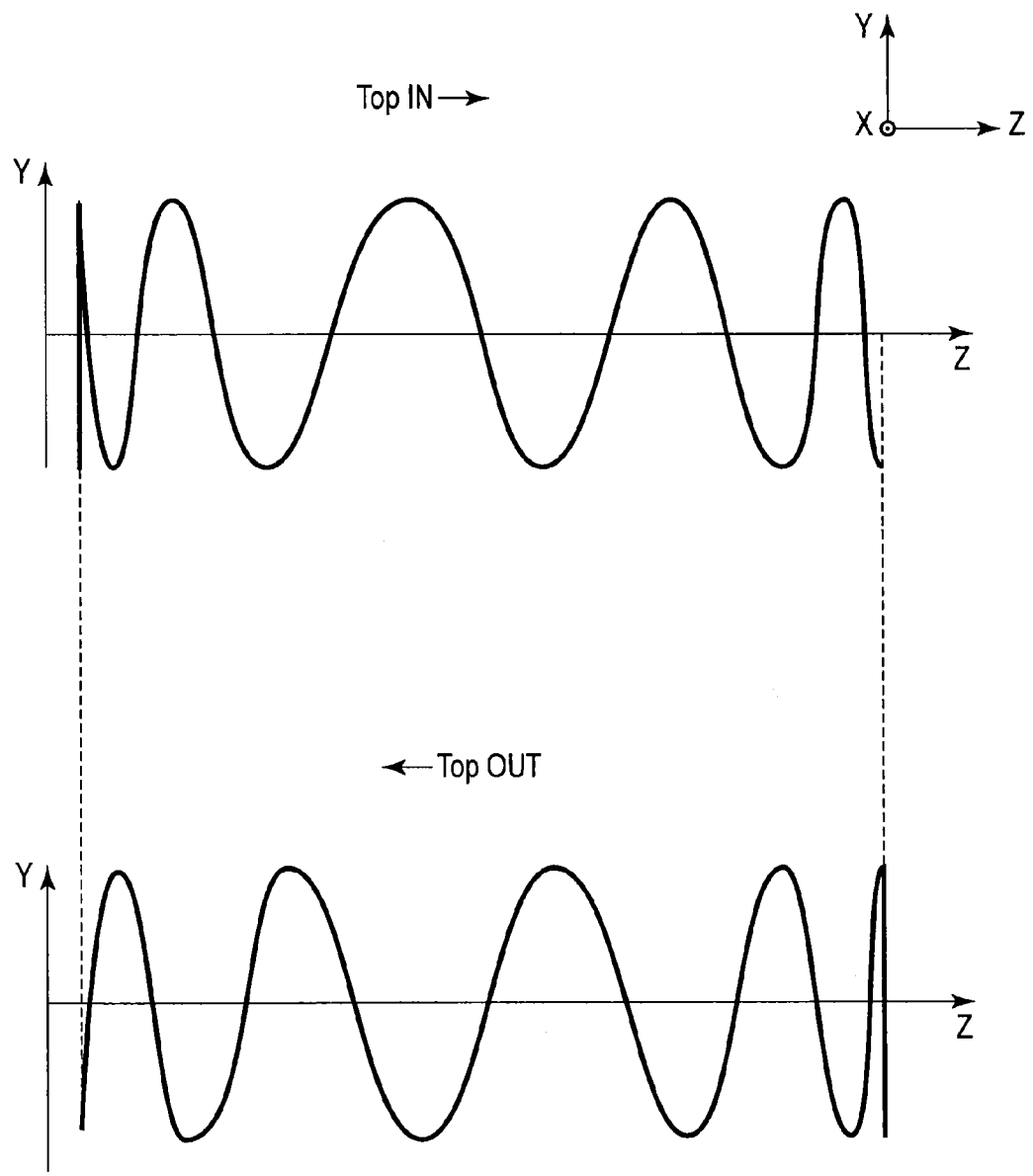
FIG. 11 is a graph showing an example of a locus of the X-ray tube or X-ray detector in reciprocal helical scanning in each moving direction of the top according to this embodiment.

FIG. 11 is a graph showing an example of a helical locus in "top IN" and a helical locus in "top OUT" when the driving control unit 38 controls the top driving unit 21 in the case of FIG. 10. The driving control unit 38 controls the top driving unit 21 so as to match helical loci with respect to the object in "top IN" and "top OUT" in reciprocal helical scanning. In other words, the driving control unit 38 performs control to match helical loci with each other in the respective reciprocal movements like the first reciprocal movement and the second reciprocal movement.

That is, a plurality of helical loci respectively corresponding to a plurality of respective forward movements in a plurality of reciprocal movements almost are matched with each other. In addition, a plurality of helical loci respectively corresponding to a plurality of respective backward movements in a plurality reciprocal movements almost are matched with each other. Note that the rotational angle of the X-ray tube 12 at the relative movement start time in a forward path may be equal to the rotational angle of the X-ray tube 12 at the relative movement start time in a backward path or may differ from it by 180°.

FIG. 12 is a view showing an example of the positional relationship between the X-ray tube 12, the X-ray detector 13, and the imaging range in reciprocal helical scanning associated with FIGS. 10 and 11. "FOV" in FIG. 12 stands for a field of view. The hatched region defined by "FOV" and the imaging range is a scan region. The driving control unit 38 controls the top driving unit 21 so as to stop the top 22 until the rotating frame 15 rotates through 360° at a turnaround point from forward scanning to backward scanning. This makes it possible to reconstruct an image at each of turnaround points (the two ends of the imaging range) by using projection data corresponding to one rotation of the rotating frame 15. This can obtain an imaging range larger than the reciprocal moving range of the top 22, as shown in FIG. 12.

FIG. 13 is a graph showing an example of the time dependencies on the rotational angle of the X-ray tube 12, the top position, and the top velocity under the control of the driving control unit 38. For the sake of descriptive convenience, FIG. 13 shows a case in which the rotational angle of the X-ray tube 12 is used instead of the rotational angle of the rotating frame 15. When reciprocal helical scanning starts, the X-ray tube 12 makes one rotation around the Z-axis while the top 22 stops moving. The top 22 then moves along a forward direction. At this time, the X-ray tube 12 makes N rotations (N is a natural number) around the Z-axis at a constant angular velocity. The top 22 stops at a turnaround time point. While the top 22 stops moving, the X-ray tube 12 makes one rotation around the Z-axis. Subsequently, the top 22 moves along a backward direction. At this time, the X-ray tube 12 makes N rotations (N is a natural number) around the Z-axis at a constant angular velocity. The top 22 stops at a turnaround time point. While the top 22 stops moving, the X-ray tube 12 makes one rotation around the Z-axis. Subsequently, the above operation repeats.

A function of implementing an improvement in temporal resolution in reciprocal helical scanning and a reduction in helical locus difference will be described below.

Figure 14:
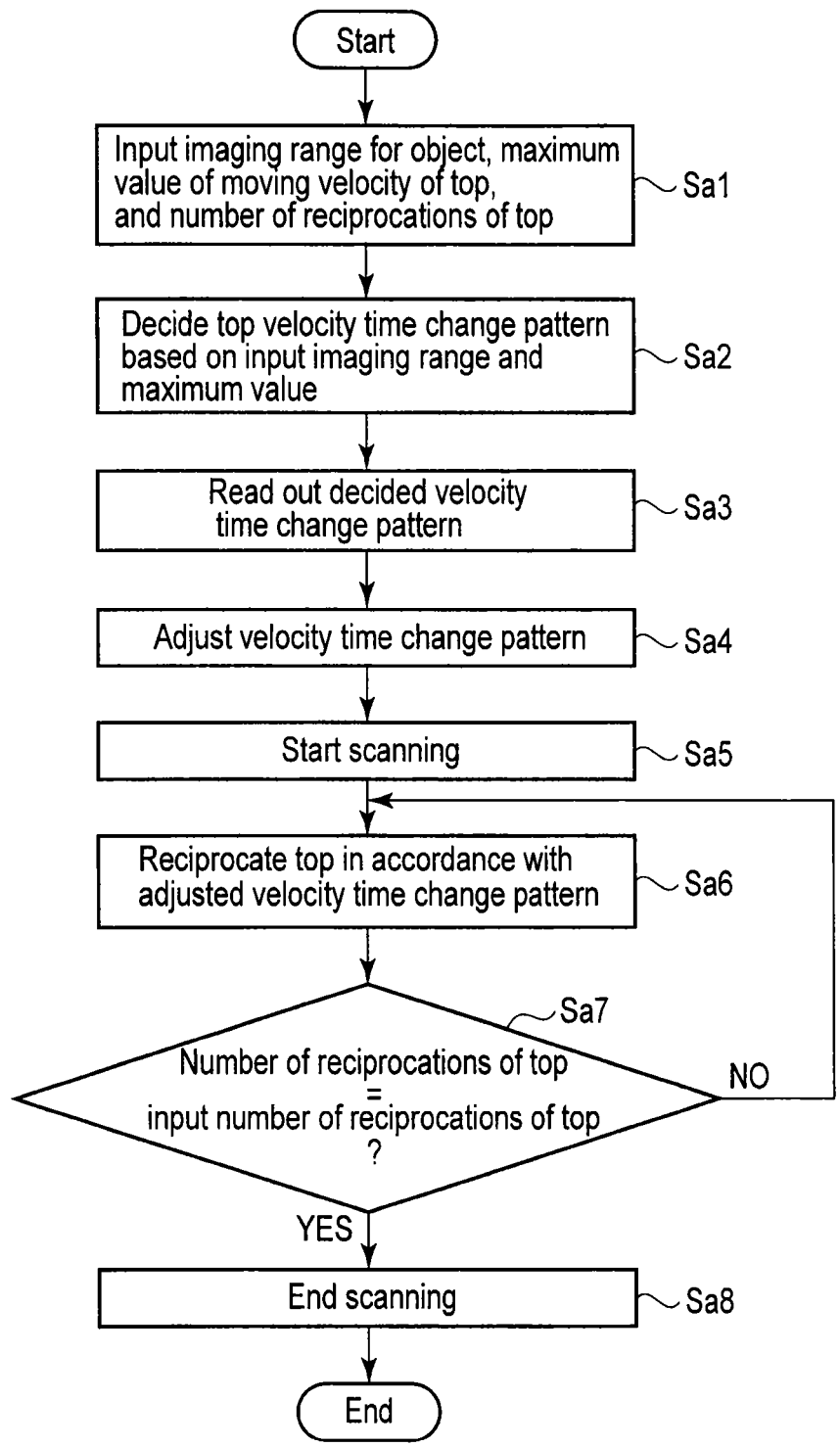
FIG. 14 is a flowchart showing an example of a procedure for reciprocal helical scanning according to this embodiment.

FIG. 14 is a flowchart showing an example of a procedure for reciprocal helical scanning.

The operator inputs an imaging range for an object, the maximum value of the moving velocity of the top 22, and the number of reciprocal movements of the top 22 via the input unit 31 (step Sa1). The apparatus then decides a top velocity time change pattern (velocity time change pattern) based on the input imaging range and maximum value (step Sa2). At this time, the operator may select imaging corresponding to one rotation at a turnaround time point in reciprocal movement of the top 22. Note that the operator can set velocity control on the top 22 via the input unit 31. The apparatus reads out the decided velocity time change pattern from the velocity time change pattern storage unit 37 (step Sa3). The apparatus adjusts the readout velocity time change pattern based on the input imaging range (step Sa4). When the apparatus starts scanning (step Sa5), the top 22 reciprocally moves based on the adjusted velocity time change pattern (step Sa6). The apparatus repeats the processing in step Sa6 until the number of reciprocal movements of the top 22 becomes equal to the input number of reciprocal movements (step Sa7). When the number of reciprocal movements of the top 22 becomes equal to the input number of reciprocal movements, the apparatus stops scanning (step Sa8).

(Modification)

FIG. 15 is a view showing the arrangement of the X-ray CT apparatus 100 according to a modification of this embodiment. As shown in FIG. 15, the X-ray CT apparatus 100 includes the gantry 10, the bed 20, and the console device 30. A difference between the arrangement of this embodiment (FIG. 1) and the arrangement of this modification (FIG. 15) will be described. The modification includes an imaging range storage unit 39 and an imaging range setting unit 40 instead of the velocity time change pattern storage unit 37 of the embodiment.

The imaging range storage unit 39 stores a plurality of discrete imaging ranges. Each of the plurality of imaging ranges is an imaging range in which the time required for one reciprocal movement of the top 22 becomes an integer multiple of the time taken to cause the rotating frame 15 to make one rotation around the rotation axis. In addition, each of the plurality of imaging ranges is an imaging range in which the stop time of the top at a turnaround time point in reciprocal movement of the top 22 becomes minimum (almost zero). The imaging range storage unit 39 stores top velocity time change patterns (velocity time change patterns) respectively corresponding to the plurality of discrete imaging ranges. Note that the imaging range storage unit 39 may store a plurality of velocity time change patterns in correspondence with the respective discrete imaging ranges.

The imaging range setting unit 40 sets, as an imaging range in which reciprocal helical scanning is to be executed (to be referred to as an execution imaging range hereinafter), an imaging range, of the plurality of discrete imaging ranges, which is equal to the imaging range input via the input unit 31 (to be referred to as an input imaging range hereinafter) or the minimum imaging range of imaging ranges exceeding the input imaging range.

Figure 16:
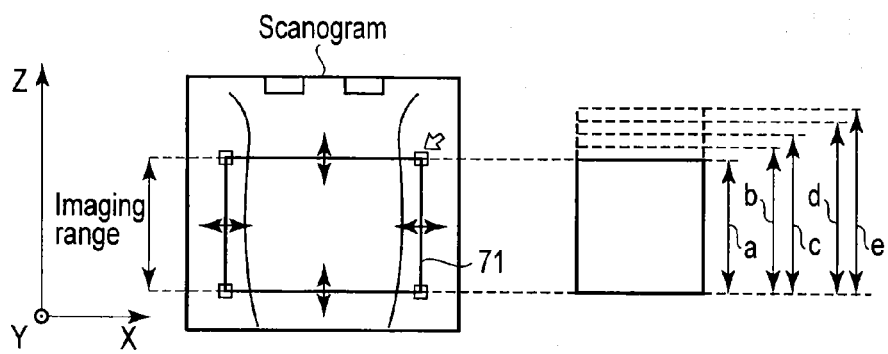
FIG. 16 is a view showing an example of the settings of an imaging range for an object according to this modification.

FIG. 16 is a view showing an example of setting an imaging range for an object according to this modification. Referring to FIG. 16, an input imaging range 71 is input by dragging on, for example, the scanogram displayed on the display unit 32 with a mouse or the like of the input devices. At this time, the imaging range setting unit 40 sets, as execution imaging ranges, a plurality of discrete imaging ranges ("a" in FIG. 16), of the imaging ranges ("a", "b", "c", "d", and "e" in FIG. 16) stored in the imaging range storage unit 39, which exceed the input imaging range 71.

Figure 17:
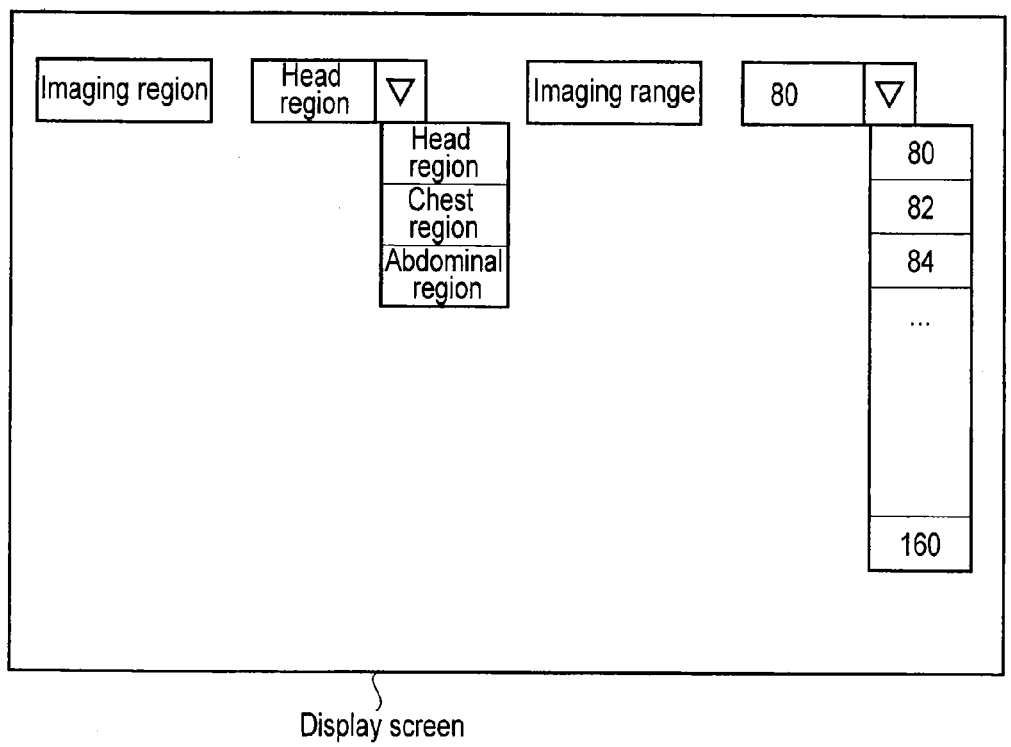
FIG. 17 is a view showing an example of a setting window for an imaging range for object according to this modification.

FIG. 17 is a view showing an example of a setting window for an imaging range for an object according to this modification. Imaging regions such as a head region, chest region, and abdominal region shown in FIG. 17 are displayed in a pull-down menu. The operator selects a desired region (the head region in FIG. 17) of the imaging regions displayed in the pull-down menu via an input device. Subsequently, the discrete imaging ranges stored in the imaging range storage unit 39 are displayed in the pull-down menu (80, 82, 84, . . . , 160 in FIG. 17). The operator selects a desired imaging range (80 in FIG. 17) of the discrete imaging ranges displayed in the pull-down menu via an input device.

A function of setting an execution imaging range will be described below.

Figure 18:
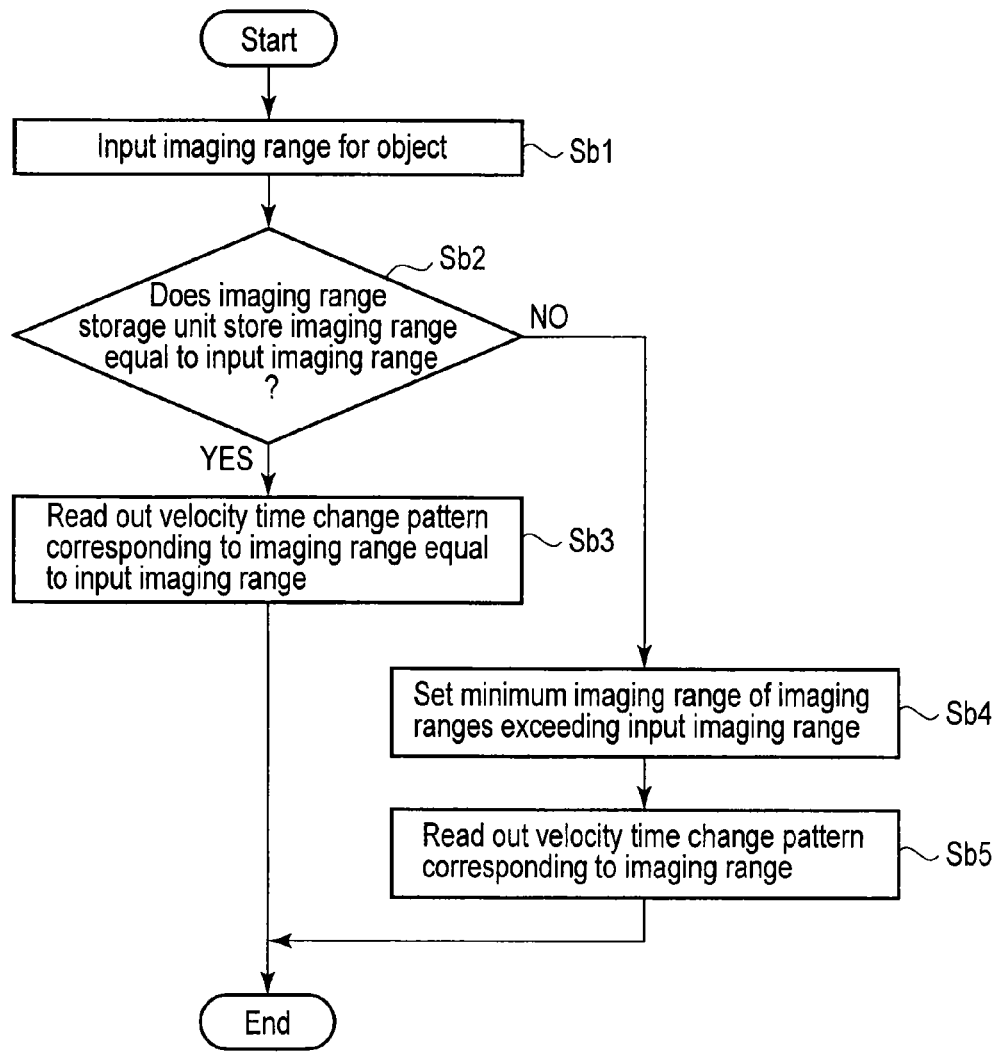
FIG. 18 is a flowchart showing an example of a procedure for setting an imaging range for reciprocal helical scanning according to this modification.
Figure 19:
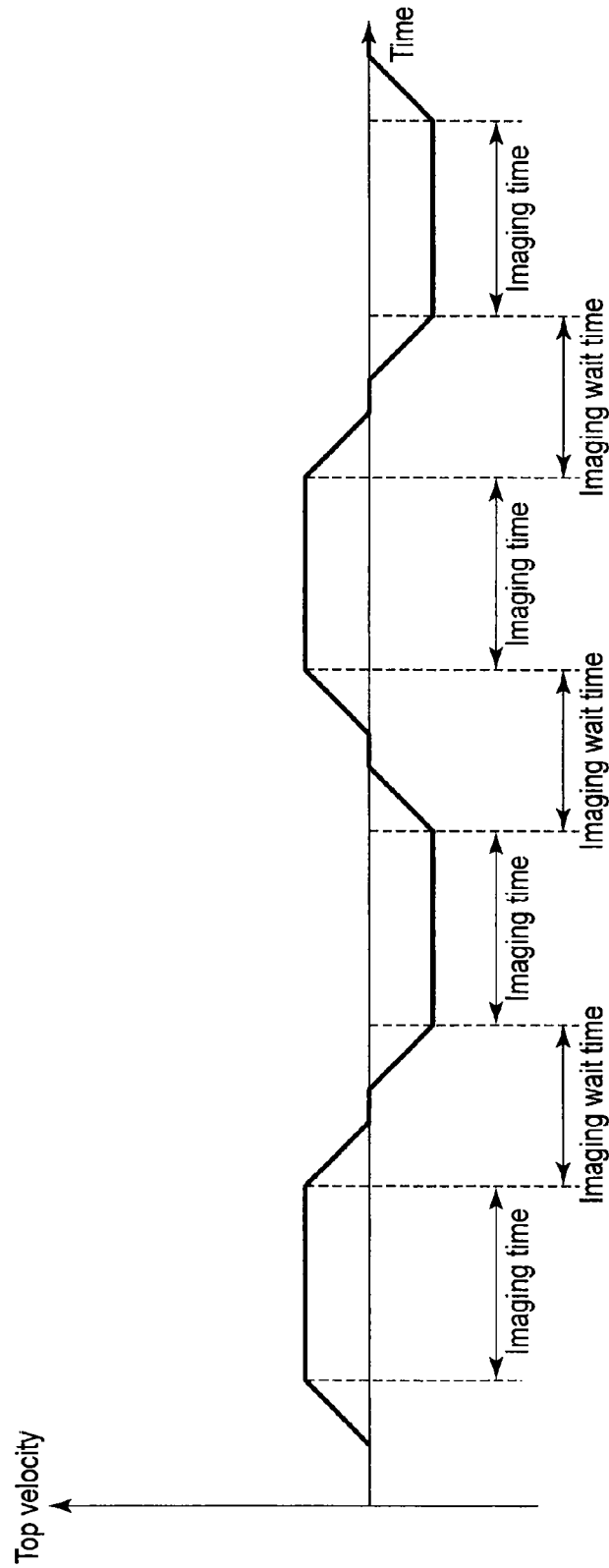
FIG. 19 is a graph showing the relationship between the time and the velocity of the top in conventional reciprocal helical scanning.

FIG. 18 is a flowchart showing an example of a procedure for setting an imaging range in reciprocal helical scanning according to this modification.

The operator inputs an imaging range for an object concerning reciprocal helical scanning via an input device of the input unit 31 (step Sb1). If the imaging range storage unit 39 stores an imaging range equal to the input imaging range 71 (step Sb2), the apparatus reads out a velocity time change pattern corresponding to this imaging range from the imaging range storage unit 39 (step Sb3). The apparatus drives the top 22 based on the readout velocity time change pattern. If the imaging range storage unit 39 stores no imaging range equal to the input imaging range 71 (step Sb2), the apparatus sets, as an execution imaging range, the minimum imaging range of the plurality of discrete imaging ranges exceeding the input imaging range 71 (step Sb4). The apparatus reads out a velocity time change pattern corresponding to the set imaging range from the imaging range storage unit 39 (step Sb5). The apparatus drives the top 22 based on the readout velocity time change pattern.

According to the arrangement described above, the following effects can be obtained.

The X-ray computed tomography apparatus 100 according to this embodiment can reduce or null the imaging wait time at each turnaround time point in reciprocal movement of the top 22 in reciprocal helical scanning. This improves the temporal resolution. In addition, it is possible to match helical loci in reciprocal helical scanning with each other in forward scanning and backward scanning. This can equalize image quality in the respective scans. As described above, it is possible to improve the accuracy of perfusion analysis. In addition, setting discrete imaging ranges concerning reciprocal helical scanning can facilitate controlling the gantry 10 and the bed 20. This makes it possible to provide the inexpensive X-ray computed tomography apparatus 100. In addition, it is possible to perform imaging in a wider range by stopping the top 22 at the two ends of the moving range of the top 22 and executing 360° or (180°+fan angle) imaging.

In addition, it is possible to reduce directional artifacts remaining in differences between forward paths and between backward paths. This can prevent deterioration in the accuracy of an analysis result on, for example, perfusion analysis.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
an X-ray tube configured to generate X-rays;
an X-ray detector configured to detect the X-rays generated from the X-ray tube and transmitted through an object;
a top on which the object is placed;
a rotation driving unit configured to rotate a rotating frame around the object, wherein the X-ray tube and the X-ray detector are mounted on the rotating frame;
a movement driving unit configured to relatively reciprocate the rotating frame and the top over a plurality of times along a long-axis direction of the top; and
a scan control unit configured to control the movement driving unit in relative reciprocal movement of the rotating frame and the top to coordinate a first plurality of moving loci of the X-ray tube with a first plurality of respective forward movements of at least one of the top and the rotating frame, and to coordinate a second plurality of moving loci of the X-ray tube with a second plurality of respective backward movements of at least one of the top and the rotating frame.

2. The X-ray computed tomography apparatus of claim 1, wherein the scan control unit is configured to determine velocity of the reciprocal movement based on imaging range information.

3. The X-ray computed tomography apparatus of claim 2, wherein the scan control unit is configured to determine acceleration of relative movement at a turnaround portion of the reciprocal movement based on the imaging range information.

4. The X-ray computed tomography apparatus of claim 3, wherein the scan control unit is configured to determine a time change pattern of acceleration based on an imaging range for the object.

5. The X-ray computed tomography apparatus of claim 2, wherein the scan control unit is configured to determine the velocity of the reciprocal movement in a constant-velocity interval based on the imaging range information.

6. The X-ray computed tomography apparatus of claim 2, wherein the scan control unit is configured to control the X-ray tube and the X-ray detector to generate the X-rays and acquire projection data in acceleration and deceleration intervals of a turnaround portion of the reciprocal movement.

\* \* \* \* \*